United States Patent
He et al.

(10) Patent No.: US 9,878,167 B1
(45) Date of Patent: Jan. 30, 2018

(54) MEDICAL IMPLANT SELECTION PROTOCOL

(71) Applicant: QUALCOMM Incorporated, San Diego, CA (US)

(72) Inventors: Linhai He, San Diego, CA (US); Osvaldo Alcala, Chula Vista, CA (US); Stephen Jay Shellhammer, Ramona, CA (US); Adam Edward Newham, Poway, CA (US)

(73) Assignee: QUALCOMM Incorporated, San Diego, CA (US)

( * ) Notice: Subject to any disclaimer, the term of this patent is extended or adjusted under 35 U.S.C. 154(b) by 0 days.

(21) Appl. No.: 15/633,522

(22) Filed: Jun. 26, 2017

Related U.S. Application Data

(60) Provisional application No. 62/433,146, filed on Dec. 12, 2016.

(51) Int. Cl.

| | |
|---|---|
| *A61N 1/37* | (2006.01) |
| *A61N 1/372* | (2006.01) |
| *A61B 5/07* | (2006.01) |
| *A61B 5/00* | (2006.01) |
| *A61B 5/0478* | (2006.01) |
| *A61N 1/05* | (2006.01) |
| *A61N 1/36* | (2006.01) |

(52) U.S. Cl.
CPC ........ *A61N 1/37288* (2013.01); *A61B 5/0478* (2013.01); *A61B 5/076* (2013.01); *A61B 5/6868* (2013.01); *A61N 1/0529* (2013.01); *A61N 1/36025* (2013.01)

(58) Field of Classification Search
CPC ............ A61N 1/36025; A61N 1/37288; A61N 1/0456; A61N 1/0529; A61N 1/0476; A61B 5/031; A61B 5/076; A61B 5/0478; A61B 5/6868; A61B 5/01; A61B 5/14539
USPC ............ 340/10.42, 572.8, 539.1; 607/46, 48
See application file for complete search history.

(56) References Cited

U.S. PATENT DOCUMENTS

| | | | |
|---|---|---|---|
| 2005/0283203 A1* | 12/2005 | Flaherty | A61B 5/04001 607/48 |
| 2009/0157141 A1* | 6/2009 | Chiao | A61N 1/36071 607/46 |

(Continued)

FOREIGN PATENT DOCUMENTS

| | | |
|---|---|---|
| WO | 2010042750 A2 | 4/2010 |
| WO | 2012126003 A1 | 9/2012 |

OTHER PUBLICATIONS

Rodriguez-Perez A., et al., "A 64-Channel Ultra-Low Power System-on-Chip for Local Field and Action Potentials Recording", Bio-MEMS and Medical Microdevices II, edited by Sander van den Driesche, Proc. of SPIE vol. 9518, 2015, pp. 1-10.

*Primary Examiner* — Ali Neyzari
(74) *Attorney, Agent, or Firm* — Kilpatrick Townsend & Stockton

(57) ABSTRACT

Techniques provided herein are directed toward providing a selection protocol that can be used in such biological measurement and stimulation systems to select only a portion of the medical implants for reporting during a particular system cycle. In particular, the interrogator device can send the first message that defines a group to the medical implants, then send a second message with the identifier of the group to trigger communications with the medical implants of that group.

30 Claims, 9 Drawing Sheets

(56) References Cited

U.S. PATENT DOCUMENTS

2015/0088224 A1 3/2015 Goldwasser et al.
2017/0020402 A1 1/2017 Rogers et al.

* cited by examiner

MEDICAL IMPLANT SELECTION PROTOCOL

RELATED APPLICATIONS

This application claims the benefit of U.S. Provisional Application No. 62/433,146, filed Dec. 12, 2016, entitled "NEUROGRAIN SELECTION PROTOCOL", of which is assigned to the assignee hereof, and incorporated herein in its entirety by reference.

BACKGROUND

A biological measurement and stimulation system for a patient can comprise an interrogator device, typically in, on, or in proximity to the patient, and a plurality of electronic medical implants that can take biological measurements of a body part (e.g., biological tissue) and communicate them to the interrogator device. The interrogator device can then communicate this information to other devices, such as a mobile phone, tablet, or medical device of the patient or patient's healthcare provider. The interrogator device can also communicate with the medical implants to cause them to stimulate the body part.

Communication between the interrogator device and medical implants may occur wirelessly via radio frequency (RF) signals. But scheduling of the medical implants' uplink transmissions (e.g., using time division multiple access (TDMA) media access control (MAC) protocol), can be difficult because number of medical implants, which can potentially range in the thousands or more. Furthermore, for various reasons, the interrogator device may not need to communicate with all medical implants during a particular system cycle.

SUMMARY

Techniques provided herein are directed toward providing a selection protocol that can be used in such biological measurement and stimulation systems to select only a portion of the medical implants for reporting during a particular system cycle. In particular, the interrogator device can send the first message that defines a group to the medical implants, then send a second message with the identifier of the group to trigger communications with the medical implants of that group.

An example method of implementing a selection protocol between an interrogator device and a plurality of medical implants of a medical implant system, according to the description, comprises sending, with the interrogator device via a local wireless interface of the interrogator device, a first message identifying at least a portion of the plurality of medical implants. The first message comprises a group identifier identifying a group and a list indicating an order in which each medical implant of the at least a portion of the plurality of medical implants is to communicate. The method further comprises receiving, from each medical implant of the at least a portion of the plurality of medical implants, a respective acknowledgement message, and subsequent to the receiving, sending, via the local wireless interface, a second message soliciting communication from each medical implant of the at least a portion of the plurality of medical implants, the second message comprising the group identifier.

In some embodiments, the method may include one or more of the following features. The group identifier may correspond to a group identifier programmed into one or more medical implants of the at least a portion of the plurality of medical implants during manufacture. The list may designate each medical implant of the at least a portion of the plurality of medical implants to the group. The list may comprise an address list, and an order of addresses in the address list is indicative of a slot index for each of the at least a portion of the plurality of medical implants to transmit data to the interrogator device. The list may comprise a list of medical implants to be turned on or off. The list may comprise a bitmap having a bit corresponding to each medical implant of the at least a portion of the plurality of medical implants, the bit indicating whether each respective medical implant is turned on or off. The bitmap may further indicates a slot index for each medical implant turned on in the bitmap. The method may further comprise, receiving, subsequent to sending the second message, data from one or more medical implants of the at least a portion of the plurality of medical implants.

An example interrogator device for implementing a selection protocol when communicating with a plurality of medical implants of a medical implant system, according to the description, comprises a local wireless interface, and a processing unit communicatively coupled with the local wireless interface. The processing unit is configured to cause the interrogator device to send, via the local wireless interface, a first message identifying at least a portion of the plurality of medical implants. The first message comprises a group identifier identifying a group, and a list indicating an order in which each medical implant of the at least a portion of the plurality of medical implants is to communicate. The processing unit is further configured to cause the interrogator device to receive, from each medical implant of the at least a portion of the plurality of medical implants, a respective acknowledgement message, and subsequent to the receiving, send, via the local wireless interface, a second message soliciting communication from each medical implant of the at least a portion of the plurality of medical implants, the second message comprising the group identifier.

In some embodiments, the interrogator device may include one or more of the following features. The interrogator device can be configured to cause the group identifier to correspond to a group identifier programmed into one or more medical implants of the at least a portion of the plurality of medical implants during manufacture. The interrogator device can be configured to cause the list to designate each medical implant of the at least a portion of the plurality of medical implants to the group. Interrogator device can be configured to include, in the list, an address list, and cause an order of addresses in the address list to indicate a slot index for each of the at least a portion of the plurality of medical implants to transmit data to the interrogator device. Interrogator device can be configured to cause the list to comprise a list of medical implants to be turned on or off and/or cause the list to comprise a bitmap having a bit corresponding to each medical implant of the at least a portion of the plurality of medical implants, the bit indicating whether each respective medical implant is turned on or off. Interrogator device can be configured to cause the bitmap to further indicate a slot index for each medical implant turned on in the bitmap. The processing unit can be configured to cause the interrogator device to, subsequent to sending the second message, receive data from one or more medical implants of the at least a portion of the plurality of medical implants.

An example apparatus for implementing a selection protocol with the plurality of medical implants of a medical implant system, according to the description, comprises means for sending a first message identifying at least a portion of the plurality of medical implants. The first message comprises a group identifier identifying a group, and a list indicating an order in which each medical implant of the at least a portion of the plurality of medical implants is to communicate. The apparatus further comprises means for receiving, from each medical implant of the at least a portion of the plurality of medical implants, a respective acknowledgement message, and means for sending, subsequent to the receiving, a second message soliciting communication from each medical implant of the at least a portion of the plurality of medical implants, the second message comprising the group identifier.

The apparatus may include one or more of the following features, in some embodiments. The apparatus may comprise means for causing the group identifier to correspond to a group identifier programmed into one or more medical implants of the at least a portion of the plurality of medical implants during manufacture and/or means for causing the list to designate each medical implant of the at least a portion of the plurality of medical implants to the group. The apparatus may comprise means for causing the list to comprise an address list, and causing an order of addresses in the address list to indicate a slot index for each of the at least a portion of the plurality of medical implants to transmit data. The apparatus may comprise means for causing the list to comprise a list of medical implants to be turned on or off. The apparatus may comprise means for causing the list to comprise a bitmap having a bit corresponding to each medical implant of the at least a portion of the plurality of medical implants, the bit indicating whether each respective medical implant is turned on or off. The apparatus may further comprise means for causing the bitmap to further indicate a slot index for each medical implant turned on in the bitmap and/or means for, subsequent to sending the second message, receiving data from one or more medical implants of the at least a portion of the plurality of medical implants.

An example non-transitory computer-readable medium, according to the disclosure, comprises instructions embedded thereon for implementing a selection protocol between an interrogator device and a plurality of medical implants of a medical implant system. The Instructions include computer code for sending a first message identifying at least a portion of the plurality of medical implants, the first message comprising a group identifier identifying a group, and a list indicating an order in which each medical implant of the at least a portion of the plurality of medical implants is to communicate. The instructions further include computer code for receiving, from each medical implant of the at least a portion of the plurality of medical implants, a respective acknowledgement message, and subsequent to the receiving, sending a second message soliciting communication from each medical implant of the at least a portion of the plurality of medical implants, the second message comprising the group identifier.

The non-transitory computer-readable medium may further comprise one or more of the following features, in some embodiments. The instructions may further comprise computer code for causing the group identifier to correspond to a group identifier programmed into one or more medical implants of the at least a portion of the plurality of medical implants during manufacture. The instructions may further comprise computer code for causing the list to designate each medical implant of the at least a portion of the plurality of medical implants to the group. The instructions may further comprise computer code for causing the list to comprise an address list, and an order of addresses in the address list is indicative of a slot index for each of the at least a portion of the plurality of medical implants to transmit data to the interrogator device. The instructions may further comprise computer code for causing the list to comprise a list of medical implants to be turned on or off. The instructions may further comprise computer code for causing the list to comprise a bitmap having a bit corresponding to each medical implant of the at least a portion of the plurality of medical implants, the bit indicating whether each respective medical implant is turned on or off.

BRIEF DESCRIPTION OF DRAWINGS

Non-limiting and non-exhaustive aspects are described with reference to the following figures, wherein like reference numerals refer to like parts throughout the various figures unless otherwise specified.

DETAILED DESCRIPTION

Several illustrative embodiments will now be described with respect to the accompanying drawings, which form a part hereof. The ensuing description provides embodiment(s) only, and is not intended to limit the scope, applicability or configuration of the disclosure. Rather, the ensuing description of the embodiment(s) will provide those skilled in the art with an enabling description for implementing an embodiment. It is understood that various changes may be made in the function and arrangement of elements without departing from the spirit and scope of this disclosure.

It will be understood by a person of ordinary skill in the art that, although the embodiments provided herein are directed toward medical applications, the techniques described herein may be utilized in other applications involving digital communication. Additionally, embodiments provided herein describe the use of "medical implants," although such implants may be utilized to gather data and/or stimulate a body part without necessarily performing a medical function. A person of ordinary skill in the art will recognize many variations.

Figure 1:
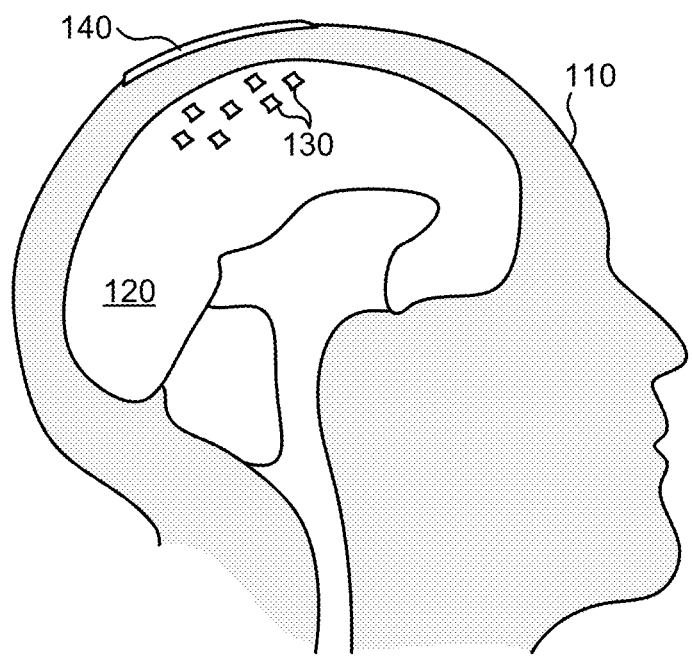
FIG. 1 is a simplified cross-sectional diagram illustrating an embodiment of a biological measurement and stimulation system.

FIG. 1 is a simplified cross-sectional diagram illustrating an embodiment of a biological measurement and stimulation system. Here, a patient's head 110 is illustrated, indicating a portion of the brain 120 in which a plurality of medical implants 130 are implanted. (For clarity, only a portion of the medical implants are labeled.) An interrogator device 140 uses low-power, short-range RF signals at a designated frequency not only to communicate with the one or more medical implants, but also, in some embodiments, to provide power to the implants. Such wireless communication can employ any of a variety of short-range wireless technologies, including near-field communication (NFC) and/or other wireless technologies. According to some embodiments, data may be communicated in a secure fashion (e.g., using any of a variety of encryption techniques).

For scenarios in which the biological measurement and stimulation system is utilized to measure and stimulate a portion of the brain (as shown in FIG. 1), the interrogator device 140 may be referred to as a "skin patch" because it may be substantially flat in shape and may be disposed on or near the patient's skin. The medical implants 130 in such scenarios may be referred to as "neurograins" because of their relatively small size and location within the patient's brain.

Depending on the application, the wireless medical implant system may comprise hundreds or thousands of medical implants 130. (Alternative embodiments may include a smaller or larger number of medical implants 130 than this.) These medical implants 130 can also communicate back to the interrogator device 140 (e.g., through RF backscatter, by changing the impedance of their respective antennas) using a time division multiple access (TDMA) protocol. The interrogator device 140 may coordinate the uplink transmission.

Medical implants 130 can comprise active devices (having a power source) and/or passive devices (having no power source) configured to take biological measurements of the brain 120 (e.g., information regarding electrical signals generated by the patient's brain cells) and communicate the measurements to the interrogator device 140 and/or provide stimulation of the patient's brain 120 (e.g., via one or more electrodes), where such stimulation may be based on communication received from the interrogator device 140. As previously noted, medical implants 130 can be powered by the interrogator device 140 using, for example, a coiled antenna drawing power from communications and/or other signals or fields generated by the interrogator device 140. It can be noted that, in alternative embodiments, the interrogator device 140 may comprise multiple antennas, and/or the biological measurement and stimulation system may have one or more nodes and/or devices between the medical implants 130 and the interrogator device 140. Because medical implants 130 can vary in functionality, they can vary in size, shape, type, and/or may have electrodes (and or other sensors) that vary as well.

Figure 8:
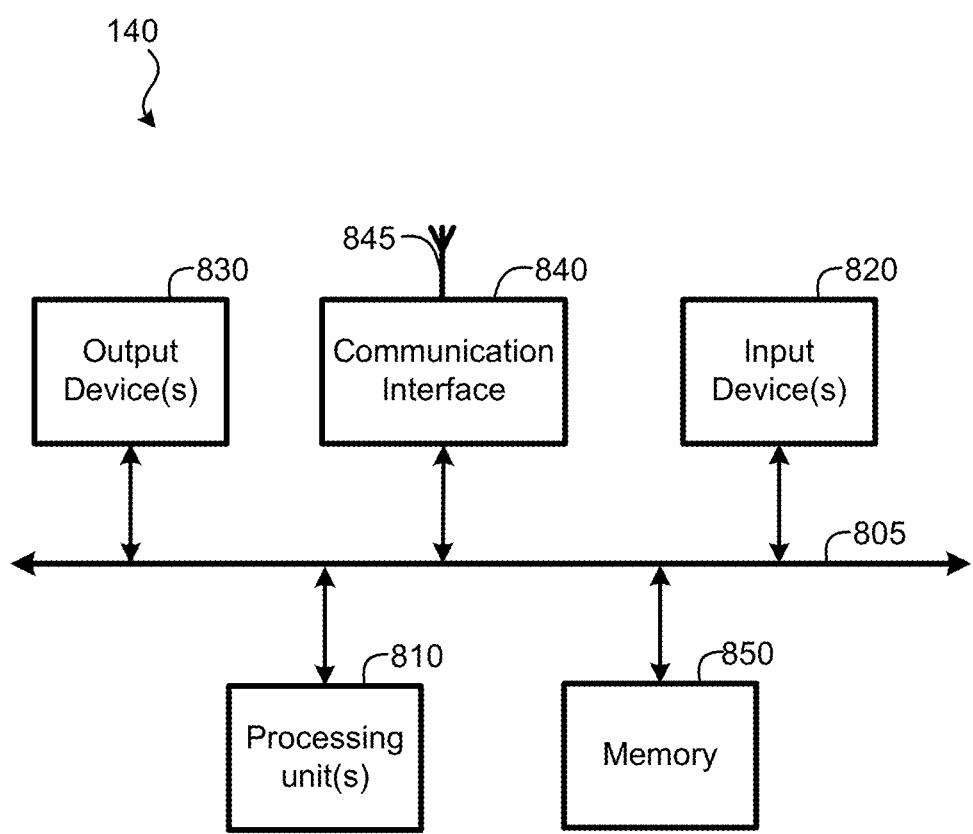
FIG. 8 is a simplified block diagram of a interrogator device, according to an embodiment.
Figure 9:
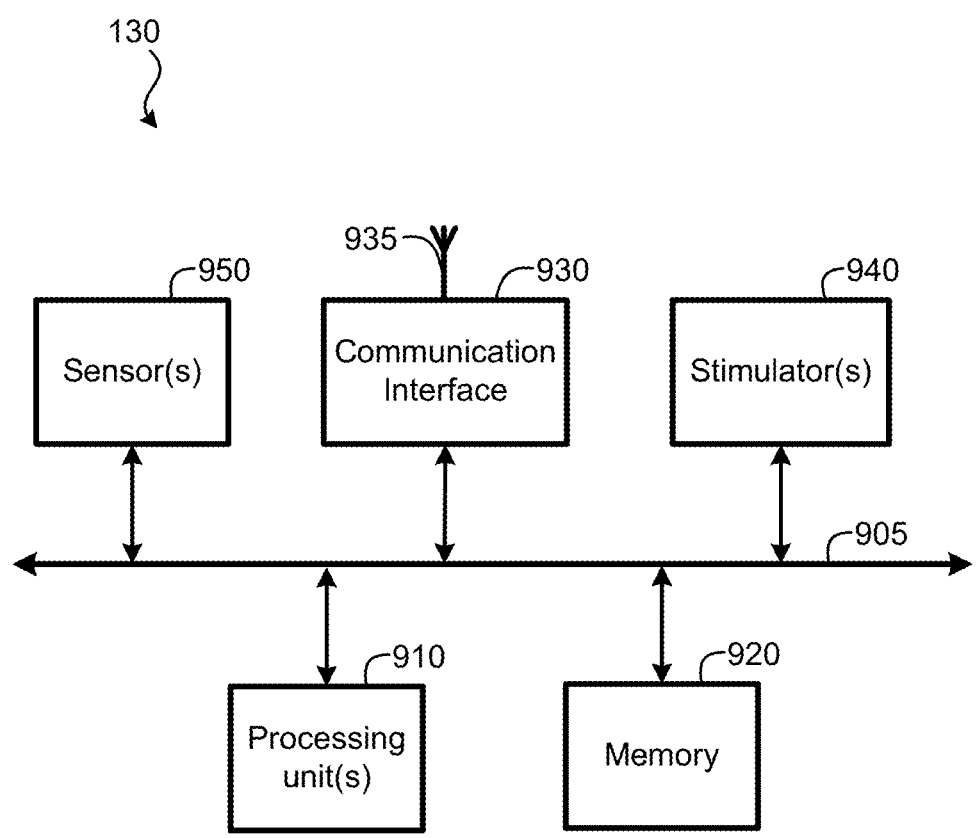
FIG. 9 is a simplified block diagram of a medical implant 130, according to an embodiment.

A person of ordinary skill in the art will appreciate the basic hardware configuration of an interrogator device 140 and/or medical implant 130. This can include, for example, a power source, processing unit, communication bus, volatile and/or non-volatile memory (which may comprise a non-transitory computer-readable medium having computer code for execution by the processing unit), transceiver, antenna, etc. The medical implant 130 may further comprise one or more sensors, electrodes, and/or stimulators utilized for sensing and/or stimulating one or more parts of the body. As such, the interrogator device 140 and/or medical implant 130 may have means for performing some, or all, of the functions described herein using one or more of its hardware and/or software components. In some embodiments, components may be selected and/or optimized for low power consumption. In particular, because medical implants 130 may be limited in size and/or power, the medical implants 130 may not have the same memory size and/or processing capabilities as the interrogator device 140. Example electrical hardware and software components of an interrogator device 140 and medical implant 130 are illustrated in FIG. 8 and FIG. 9, respectively, and described in more detail below.

Figure 2:
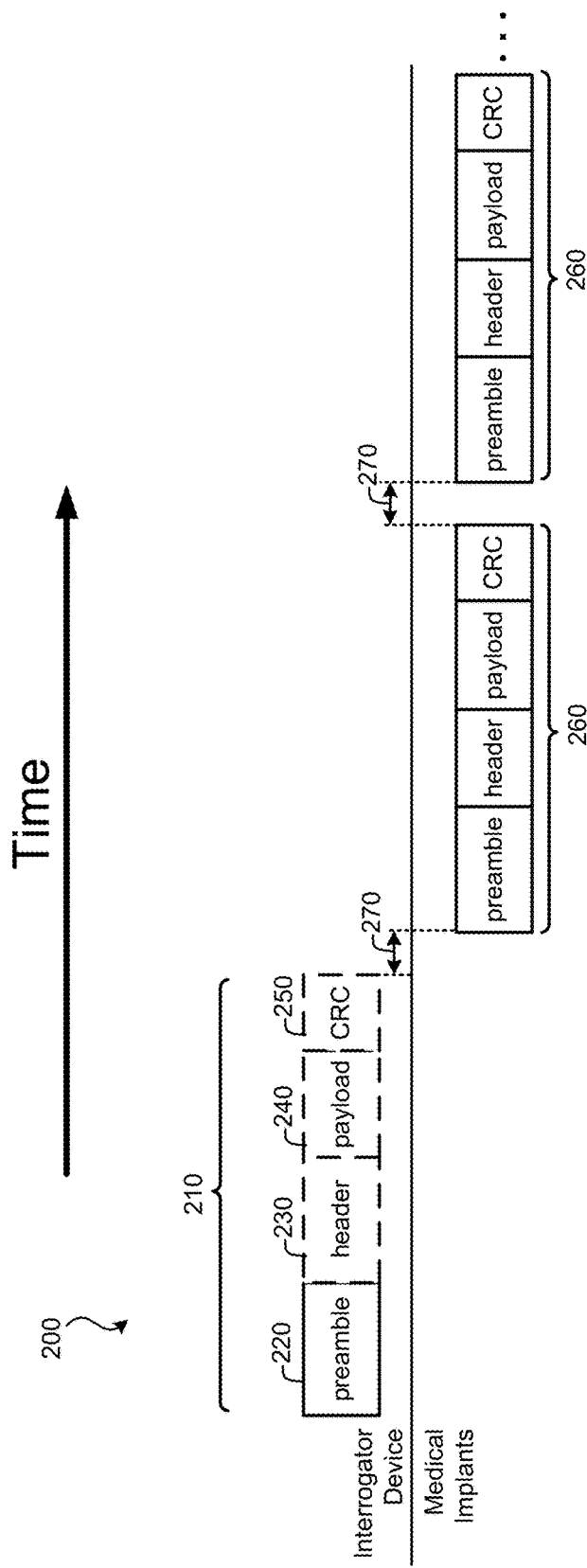
FIG. 2 is an illustration of an example system cycle, showing communications between an interrogator device and medical implants of a biological measurement and stimulation system, such as the a biological measurement and stimulation system shown in FIG. 1.

FIG. 2 is an illustration of an example system cycle 200, showing communications between the interrogator device and medical implants. In particular, the system cycle 200 utilizes a TDMA-based MAC protocol in which a downlink message 210 is first broadcast from the interrogator device to indicate the beginning of the system cycle 200. As illustrated, the downlink message 210 may include subframes such as a preamble 220 and, optionally, a header 230 (which can identify a message type of the downlink message 210), payload 240 (which may include information, such as control and/or configuration data, for some or all of the medical implants), and/or cyclic redundancy check (CRC) 250.

Based on the message received, the medical implants each learns whether it should transmit in the current system cycle 200, and if so, which time slot it should transmit in. The medical implants selected to transmit in the current system cycle 200 then each respectively transmit an uplink message 260 one by one in a preconfigured order. As indicated in FIG. 2, the uplink message 260 may include subframes similar to those of the trigger message, but with data specific to the respective medical implant. Such data for a particular medical implant can include, for example, biological measurement data captured by the medical implant. In some embodiments, uplink messages 260 may be uniform in size, and all medical implants may transmit at the same data rate, thereby ensuring a uniform length of a system cycle 200. The number of time slots available for uplink messages 260 in a system cycle may be limited to latency limits and/or other factors (but may be predetermined). In some embodiments, a "guard interval" 270 be included in the system cycle 200 as a time buffer between messages. Depending on desired functionality, the system may execute multiple system cycles, each with a different subset or group of medical implants, which may be selected using the techniques for medical implant selection provided herein below.

The length of the system cycle 200 can vary depending on capabilities of the medical implants and/or interrogator device, number of messages communicated during the system cycle 200, and/or similar factors. In an example embodiment, the entire system cycle can be approximately 100 ms, and may have time slots allocated for 1000 medical implants to send uplink messages 260.

Different groups of medical implants may communicate with the interrogator device during different system cycles. And although these groups may be predefined, it can be desirable to enable the interrogator device to dynamically define groups with which it communicates during a given system cycle. Selecting a set of medical implants in this matter can be helpful in a variety of scenarios. For example, a patient may have 1000 medical implants, but the brain biological measurement and stimulation system may have fewer than 1000 time slots for medical implant reporting in a given cycle, thus, it may be beneficial to only receive information from a subset of the medical implants at a time. (That said, as described in more detail below, groups may be divided into different "segments" to enable the group of medical implants to communicate over the course of multiple system cycles, one segment at a time.) Additionally or alternatively, some medical implants may not be able to provide any useful information (e.g., they may be defective, inactive, or not have any new data to report, etc.), in which case it is useful to select only the medical implants for reporting that are likely to have useful information. In some situations, the interrogator device may only want to receive information and/or control stimulation using a subset of the medical implants corresponding to a particular area of interest within the body part (e.g., a certain region of the brain), in which case the interrogator device may only want to receive information from that subset of medical implants. Embodiments may be based on additional or alternative reasoning for addressing only a subset of medical implants.

Techniques described herein below provide a selection protocol to enable this functionality. In particular, the techniques enable the interrogator device to define a group of medical implants in a first "schedule" message by identifying the medical implants to associate to the group. Subsequently, the interrogator device can send one or more "trigger" messages to communicate with of the medical implants of the group. Both schedule and trigger messages can be communicated in a system cycle in a manner similar to FIG. 2. Thus, the techniques herein enable a biological implant system to, during operation, dynamically assign groups of medical implants with which it communicates.

According to some embodiments, the interrogator device and medical implants may communicate using a default communication scheme upon system boot up. It may continue to communicate using this scheme (in which each medical implant may have a predetermined time slot for uplink communications, communicating in the general manner shown in FIG. 2) until the interrogator device sends a scheduled message and begins defining groups other than the default.

Figure 3:
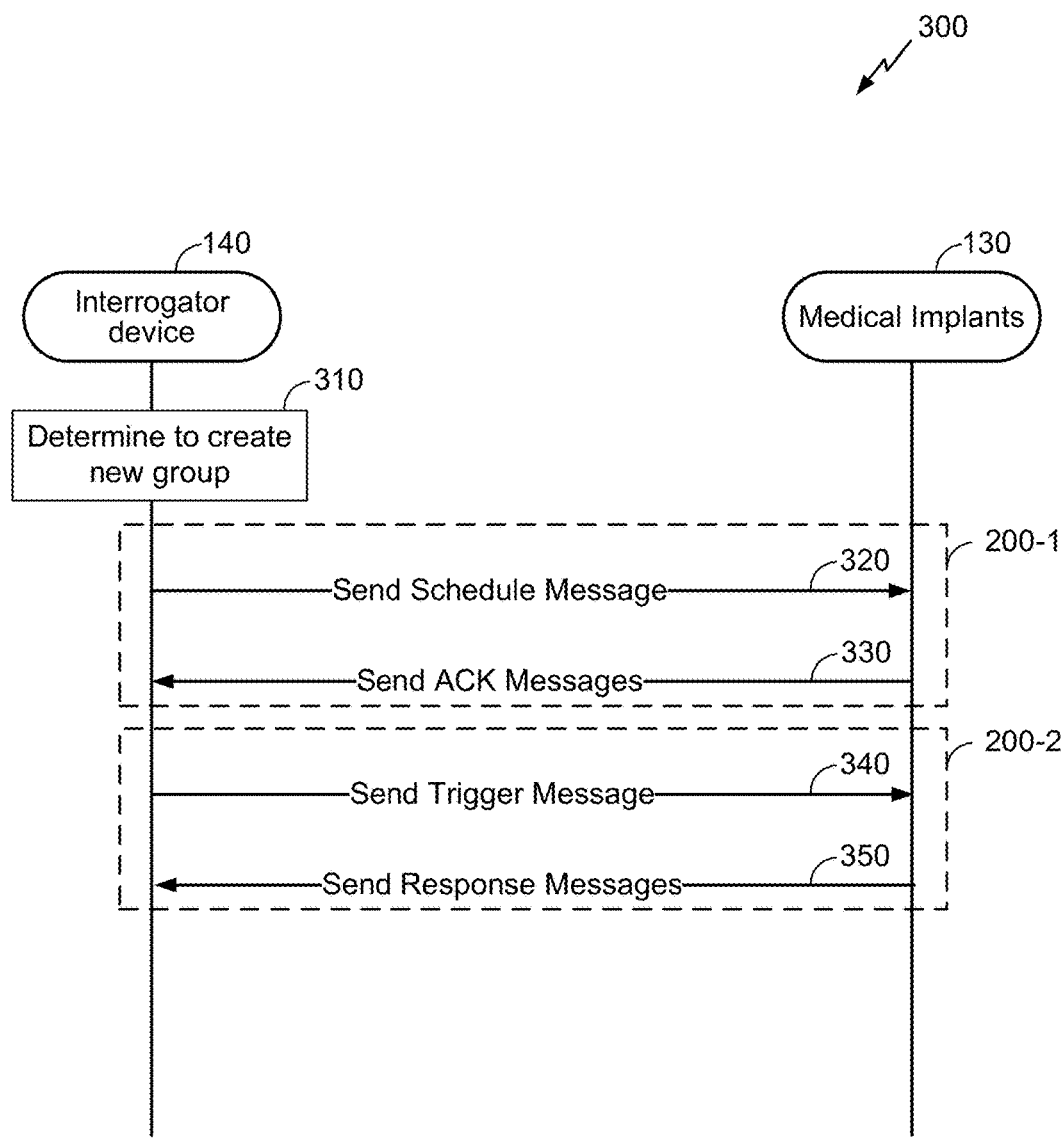
FIG. 3 is a call flow diagram generally illustrating how the of selection protocol techniques for medical implants may be implemented, according to an embodiment.

FIG. 3 is a call flow diagram 300 generally illustrating how the of selection protocol techniques for medical implants may be implemented, according to an embodiment. Here, medical implants 130 are represented by a single line, and it will be understood that messages sent by the medical implants 130 will be sent in such a manner to minimize or eliminate interference between medical implants 130 (using, for example, a TDMA protocol).

The techniques generally begin at block 310, where the interrogator device 140 determines to create a new group of medical implants 130. This determination can be made in any of a variety of ways, depending on desired functionality. As previously noted, the interrogator device 140 may be in communication with another device (a medical device, tablet, mobile phone, etc.) that may provide the interrogator device 140 with an instruction or other information causing the interrogator device 140 to determine to create the new group. Additionally or alternatively, the interrogator device 140 in itself may determine to create the new group. As noted above, this determination can be based on a variety of factors such as whether the interrogator device 140 is able to communicate with certain medical implants 130, a particular region of the body in which the medical implants of the new group are located (enabling the interrogator device 140 to create the new group to target data collection and/or stimulation of the particular region), and the like.

Was this determination is made, the interrogator device 140 can then send the schedule message at action 320. As provided in more detail below, the schedule message can include an identifier, or "group ID," for the new group, as well as an identification of which medical implants 130 are included in the new group. In some embodiments, the medical implants 130 may include a unique permanent address (which may be programmed or otherwise hard coded into the medical implant during manufacture), which can be used during communications (such as the schedule message) to identify the medical implant. In some embodiments, the addresses in a biological implant system may be less than what is in the total address space. For example, addresses may be 16 bits long (capable of tens of thousands of unique addresses), but the implant system may include only 1000 medical implants. (Other embodiments may utilize addresses that are longer or shorter, depending on desired functionality.) Thus, embodiments may not necessarily have medical implants with contiguous addresses.

The schedule message can also include an indication of the order in which the medical implants are to communicate in subsequent communications from the medical implants of the new group. That is, the schedule message can indicate a time slot for each medical implant of the new group to use. Additional details are provided herein below.

The schedule message may also include a segment number for large groups that may not be able to complete uplink communications in a single system cycle. For example, if a single system cycle has 1000 time slots, but the new group created in the schedule message has 2500 medical implants, the interrogator device may divide the new group into three segments, or subgroups (e.g., two segments of 1000 and one segment of 500). Subsequent communications with the group can take place over the course of three system cycles (one segment per cycle) so that each of the medical implants in the new group has an opportunity to provide an uplink message. A segment number may simply comprise a sequence number, indicating an order of the segments. (The segment numbers in the earlier example, then, may comprise 1, 2, and 3, indicating the order of the cycles in which each segment of medical implants would communicate.)

Medical implants 130 assigned to the new group can store the group ID (and time slot assignment, also referred to herein as a "slot index") in local memory to enable each medical implant 130 to later identify the group(s) is a part of. In some embodiments, groups may not be mutually exclusive. In such embodiments, each medical implant 130 may be part of more than one group, if so assigned.

After receiving the schedule message, the medical implants 130 respond by sending acknowledgment (ACK) messages at action 330. In some embodiments, after receiving a schedule message, the medical implant can send an ACK in its uplink transmission to the interrogator device (e.g., in the header of the uplink message 260) if it is currently active or it has been selected in the new schedule. In some embodiments, after receiving a schedule message at block 130, the medical implant can first calculate its uplink transmission slot (and the start time of the uplink transmission slot), allowing the medical implant to, during its assigned uplink transmission slot, transmit an ACK (e.g., a frame with the ACK flag in the frame header set to indicate that it has received the schedule message). In some embodiments, the sending of the schedule message at action 320 and the sending of the ACK messages at action 330 may take place in a first system cycle 200-1.

Once the group has been established (e.g., once all the interrogator device 140 receives ACK messages from all affected medical implants 130), the interrogator may then communicate with the newly-established group by sending a trigger message at action 340, triggering response messages from medical implants of the group at action 350. In addition to including the group identifier (to identify that the trigger message applies to the group), the trigger message may also include other information such as instructions for one or more medical implants 130 of the group. If the interrogator device does not receive ACK messages from all affected medical implants by the end of a system cycle, it can retransmit the schedule message unless a maximum number of retransmissions has been reached. In some embodiments, the time slots defined in the schedule message at action 320 do not take effect until the trigger message is sent at action 340 (rather than during the sending of ACK messages at action 330). Additionally or alternatively, in some embodiments, the trigger message may have an expiration such that, if the trigger message is not received by a medical implant (e.g., due to transmission error) before the expiration of the trigger message, the medical implant does not transmit in that system cycle. In other words, in some embodiments, if a medical implant is selected in a schedule message, it will send back an ACK. In the subsequent cycles, if the medical implant receives a schedule message, it should send back an ACK. If the medical implant receives a trigger message, it should start sending data. If the medical implant does not receives anything from the interrogator device, then it should not send back anything.

The medical implants 130 of the group can then send response messages at action 350, when each medical implant 130 of the group sends a uplink message (which may include data unique to the respective medical implant) during a time slot allocated to the respective medical implant. In some embodiments, the trigger message can be sent in the system cycle 200-2 following the system cycle 200-1 in which the schedule message is transmitted. Subsequent communications with the newly-formed group (e.g., in subsequent system cycles) may also be made without retransmitting the schedule message by transmitting a trigger message with the group ID, repeating the process illustrated in system cycle 200-2. In this manner, the interrogator may form many different groups and alternate communications with various groups once the groups have been formed.

As previously indicated, a schedule message can identify the medical implants of a newly-defined group. Medical implants can be identified using addresses or other unique identifiers of the medical implants. In some embodiments, the schedule message may also indicate the order in which the medical implants of the newly-defined group can transmit uplink communication. In other words, the schedule message can comprise a list (e.g., an address list or bitmap) that may indicate a time slot ("slot index") for each medical implant to use when transmitting data to the interrogator device during a system cycle starting with a trigger message for the group sent by the interrogator device. This can be done in any of a variety of ways, depending on desired functionality. Below are some examples of medical implant selection methods, according to embodiments.

Preconfigured Group Method

Under the preconfigured group method, groups are configured at the time of manufacturing and a medical implant stores identifiers for the one or more groups to which it belongs in its hardware. The corresponding schedules can also be predefined, such that if a particular group ID is included in a triggering message, each medical implant will have a corresponding pre-configured time slot for transmitting data. Under this method, there is no need for an interrogator device to send a scheduling message because everything is preconfigured. The interrogator can simply communicate with a group of medical implants by sending a trigger message with of the corresponding group ID.

Sub-Addressing Method

Another method is the "sub-addressing method." According to this method, the schedule message can include an address list that comprises the addresses of medical implants selected for the group. The position of a medical implant's address in the list indicates the time slot for that medical implant. In other words, the order of the addresses in the address list of the schedule message indicates the order in which the medical implants of a group will send uplink messages after a trigger message to the group.

Figure 4:
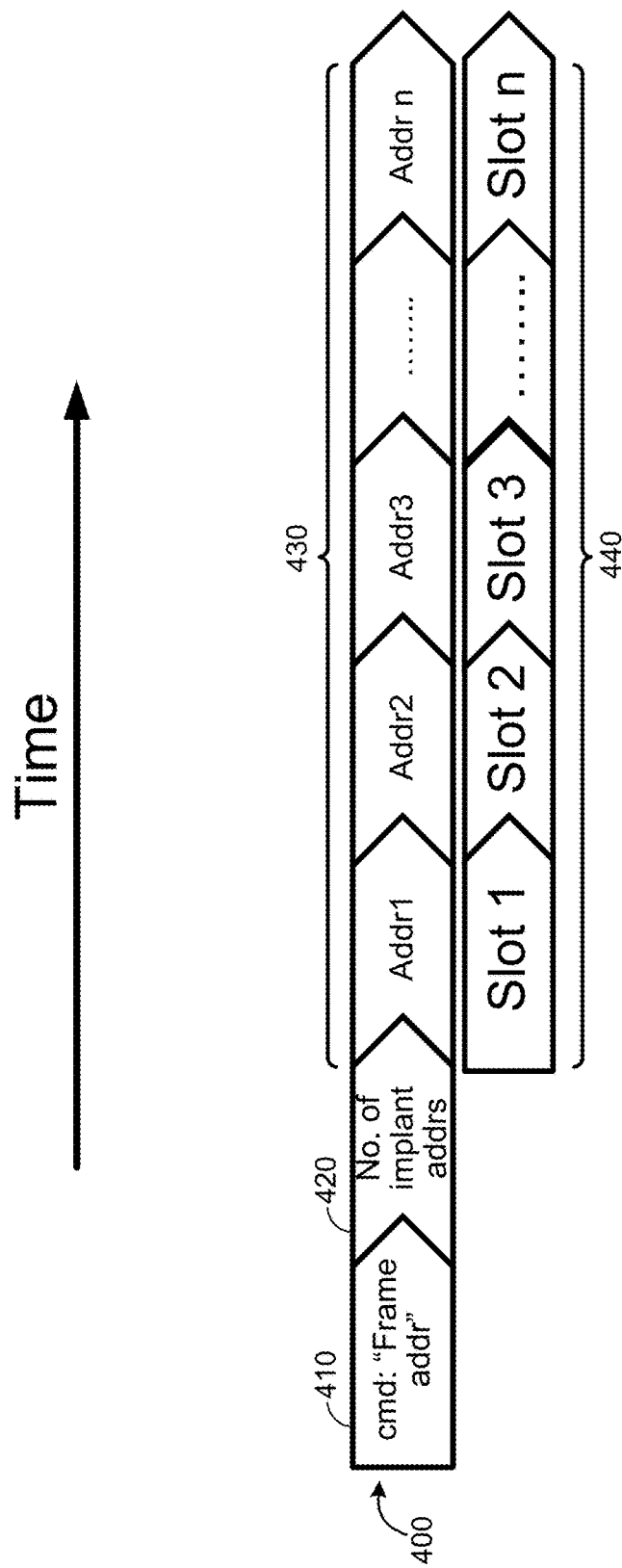
FIG. 4 is a diagram providing a visualization of how of how medical implant selection can work using a sub-addressing method, according to an embodiment.

FIG. 4 is a diagram providing a visualization of how this works, according to an embodiment. Here, a sub-addressing frame 400 (which may be part of a scheduling message) transmitted by an interrogator device includes several fields, beginning with a "frame address" command field 410. This field can serve as a flag, indicating to medical implants receiving the schedule message that address selection fields will follow. This field can be followed by a number field 420 indicating the number of medical implant addresses included in the address list, essentially telling receiving medical implants how long the list will be. (In the example of FIG. 4, the address list for 30 has n addresses, so the number field 420 would have the value of n.)

The address list 430 then follows. In the example of FIG. 4, the address list comprises n addresses corresponding with n time slots during which the respective medical implant will communicate. The medical implant having the first address in the address list 430 will get the first time slot, the medical implant having the second address in the address list 430 will get the second time slot, and so forth. In a subsequent system cycle when the interrogator device transmits a trigger message with the group ID of the group defined by this the schedule message, the medical implants will each transmit an uplink message, one after the other, in its respective time slot.

For its part, each medical plant can determine its time slot by counting the number of addresses in the address list 430 that precede its address. More specifically, when the medical implant receives the "frame address" command field 410, it is put on alert that the sub-addressing method is being utilized and an address list will follow. The medical implant can then store the number of medical implants being addressed (conveyed in number field 420), and begin counting (e.g., using a simple hardware or software counter) the addresses in the address list 430. For each address received, the medical implant can first determine whether the received address is the address of the medical implant. If not, the medical implant can then determine if the counter has reached the stored value of the number of medical implants being addressed. If so, the address list 430 has finished, and the medical implant can go to standby. If not, the medical implant can increment its counter by one and analyze the subsequent address. If the medical implant determines that the received address is the medical implants address, it can store the value of the counter as the time slot for uplink communications by that medical implant, and wait for a trigger message from the interrogator device. If each medical implant in the address list 430 executes this method, each will correctly communicate in time slots 440 having the same order as the list of addresses in the address list 430.

Individual Selection Method

The individual selection method involves using an address list similar to the address list of the sub-addressing method above. However, in the individual selection method, the address list includes a list of medical implants to be turned off or on. Because activating and/or deactivating medical implants within a group can change the time slots of the medical devices in the group, the affected medical devices can adjust their time slots accordingly.

For example, the interrogator device may first to define a group in a schedule message by including the addresses of all the medical devices of the group. The interrogator device can subsequently add medical devices to and/or remove medical devices from the group by including them in an address list of a subsequent scheduling message with the same group ID. And all medical devices affected by the change will recalculate their time slots. For instance, if the medical device having the first time slot of an existing group is removed, all remaining medical devices of the group will adjust their time slots (each subtracting they are slot index by one).

According to the individual selection method, the time slots for the medical implants of the group are based on the value of the addresses of the medical implants. For example, the medical implant having the lowest-value address will have the first time slot, the medical implant having the next-lowest-value address will have the second time slot, and so forth. (Alternatively, the order could go from highest to lowest value address, depending on desired convention.)

Figure 5:
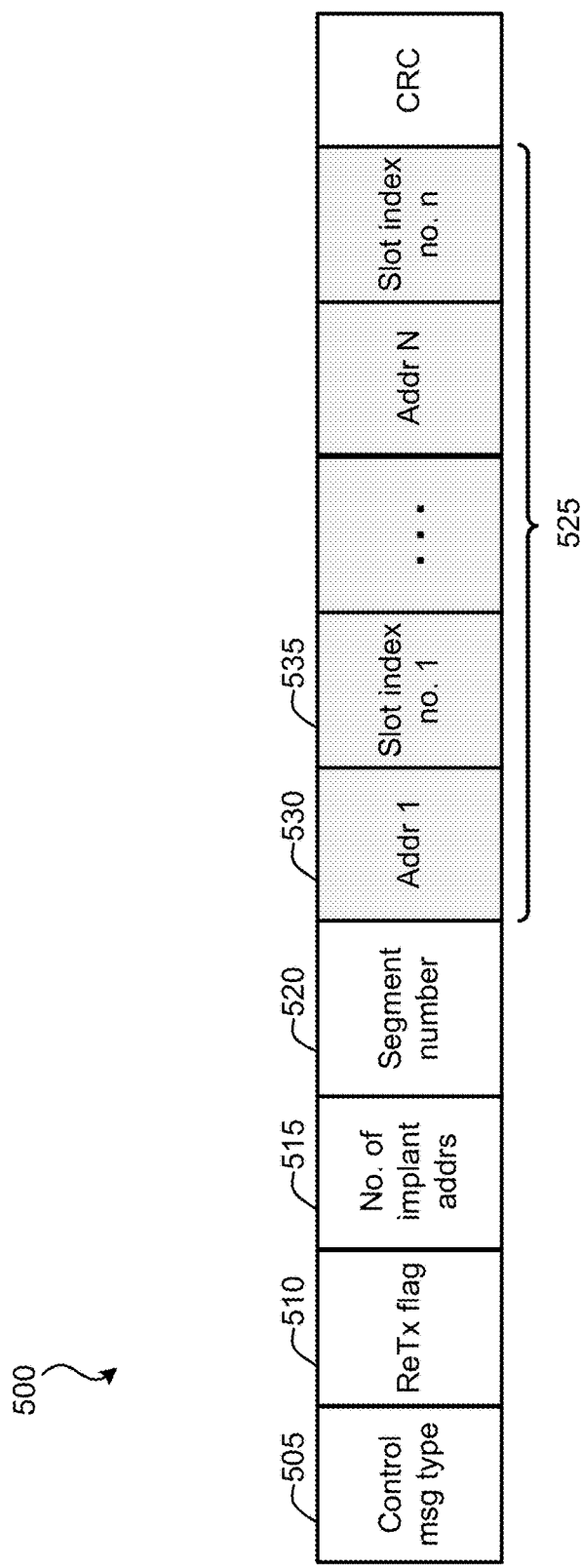
FIG. 5 is example communication frame communicated by an interrogator device to medical implants in accordance with the individual selection method of medical implant selection, according to an embodiment.

FIG. 5 is example communication frame 500 communicated by an interrogator device to medical implants in accordance with the individual selection method, according to an embodiment. The communication frame 500 may comprise or be included in a schedule message transmitted by the interrogator device. Here, the communication frame 500 begins with a control message type field 505 indicating the type of message (e.g. a schedule message, optionally specifying the use of the individual selection method). The following retransmission "ReTx" flag field indicates whether the communication frame 500 is a retransmission of an earlier transmission, and the number field 515 includes the number of implant addresses in the following address list 525. The segment number field 520 can indicate the use of multiple segments for a group, if needed, as previously described.

The address list 525 then follows. Here, the address list includes the address and corresponding slot index of each medical device in the list. For example, the "Addr 1" field 530 includes an address of a first medical device, and the following "Slot index no. 1" field 535 has slot index for the first medical device. The address list 525 will continue to have addresses and slot indexes for each address in the address list 525. The slot index includes a value indicating whether a medical devices added to or removed from the group. For example, a slot index value of zero may mean the medical device with the corresponding address is being removed from the group, where a nonzero slot index value means the medical device with the corresponding address is being added to the group. The interrogator device can keep sending the communication frame 500 until it receives ACK messages from all the affected medical implants, or its maximum retransmission limit has been reached. If the interrogator device receives ACK messages from all the affected medical implants, it can then effectuate the new schedule by broadcasting a trigger message. It can be noted that, because the Individual Selection Method can be used after a group has been established by other group-selection methods described herein (e.g. bitmap method), a group ID may not be included within the communication frame 500 (as illustrated in FIG. 5).

Similar to the sub-addressing method, medical devices can calculate their time slot in the individual selection method from the address list. As previously noted, the order of the slots may correspond to the value of the addresses (e.g., lowest to highest), so each medical device can analyze the addresses in the address list 525 and, for any addresses with earlier time slots, the medical device can adjust its time slot accordingly. More specifically, for embodiments in which time slots are in ascending order of address value (the lowest address beginning first), the functionality performed at each medical device can go as follows: for each address in the address list (starting with the first) the medical device can determine whether the addresses lower than its own. If it is, and it is being turned off (e.g., the slot index value is zero), then the medical device can decrease the value of its existing time slot by one. Otherwise, the medical device increases the value of its existing time slot by one. If an address matches the address of the medical device, the medical device can change its function in accordance with the slot index value and stop processing the rest of the message. If the address is higher than the address of the medical device, the medical device can also stop processing the rest of the message. The value of the medical device's time slot at the end of the message (after adjusting the time slot based on the addresses in the address list) is the final value of the time slot for the medical device. If the medical device receives a retransmission of the message (as indicated in the ReTx flag field 510), the medical device can simply send an ACK message, but does not need to further adjust its time slot.

Bitmap Method

The bitmap method involves using a bitmap rather than an address list to identify the medical devices selected in a group and the time slots for the selected medical devices. Each bit in the bitmap corresponds to a medical device, and the value of the bit indicates whether the medical device is included in the group. (E.g., a "1" may indicate that the medical devices selected, and a "0" may indicate that the medical devices not selected.) Each medical device may calculate its time slot by counting the number of active medical devices (e.g., the number of "1s") before it, similar to the calculation of the time slots in the individual selection method.

Figure 6:
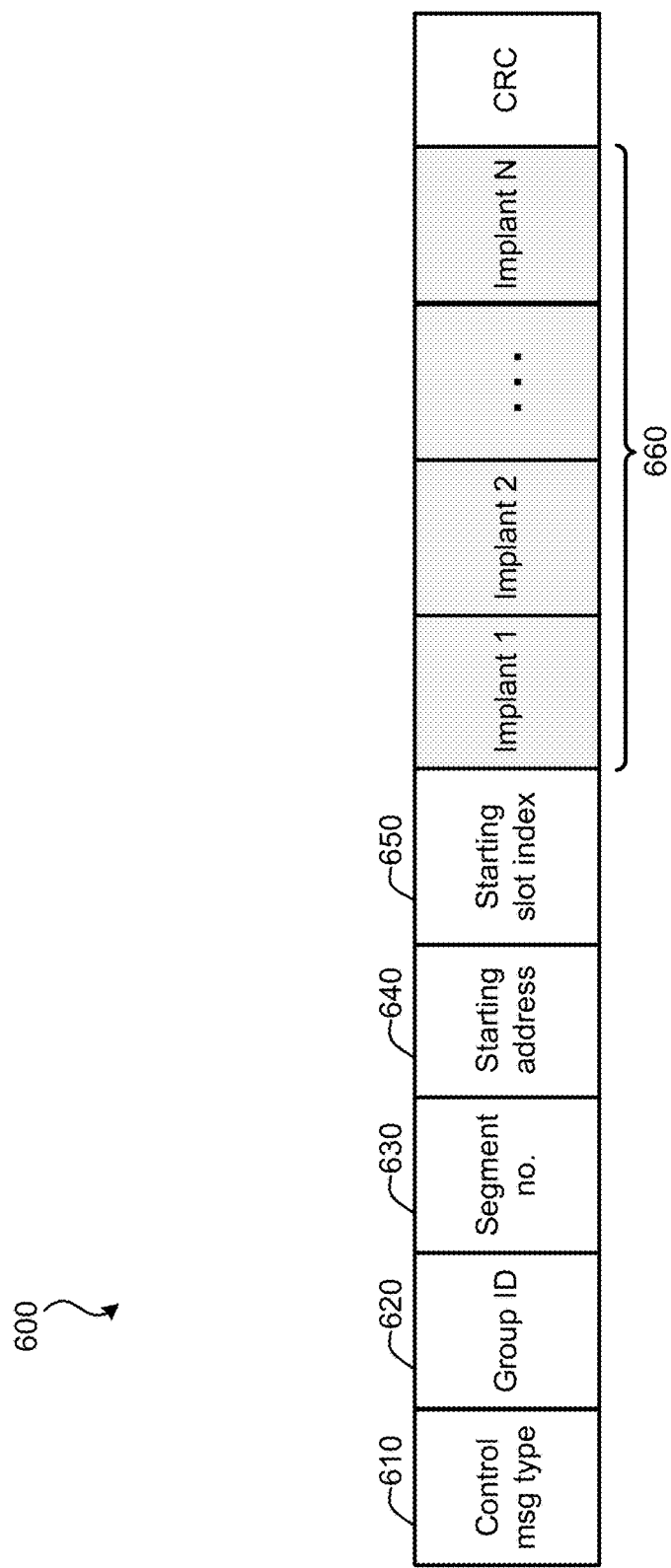
FIG. 6 is example communication frame communicated by an interrogator device to medical implants in accordance with the bitmap method of medical implant selection, according to one embodiment.

FIG. 6 is example communication frame 600 communicated by an interrogator device to medical implants in accordance with the bitmap method, according to one embodiment. The communication frame 600 may comprise or be included in a schedule message transmitted by the interrogator device. Here, the communication frame 600 begins with a control message type field 610 (which may optionally specifying the use of the bitmap method).

The fields that follow can be useful in scenarios in which a group may have multiple segments. The segment number field 630 can indicate which segment of the group the communication frame 600 applies to, the starting address field 640 can indicate which addresses first in the bitmap where multiple segments are used, and the starting slot index field 650 is used to convey the value of the starting slot index when multiple segments are used. Additional details regarding these fields are provided below.

The bitmap 660 comes next. Here, each bit in the bitmap 660 corresponds to a medical implant, and the value of the bit indicates whether the medical implant is included in the group identified by the group ID field 620. For example, where a bit as the value of "1," the medical implant corresponding to the bit is included in the group, but if the bit has a value of "0," the medical implant corresponding to the bit is not included in the group. Here, the bitmap is predetermined so that the interrogator device and medical implants can each identify which bits corresponds to which medical implants.

To determine its time slot, each medical device can keep track of the slot index, which is a running total of the amount of time slots taken (medical devices included in the group), up to and including the bit corresponding to the medical device. For example, in an embodiment in which bits having the value of "1" are added to the group and the value of the first three bits of the bitmap 660 are "101," the medical device corresponding to the third bit in the bitmap 660 will keep track of the slot index by adding the number of 1's up to and including the third bit using, for example, a simple hardware or software counter. The counter would increase with the first "1," not increase with the following "0", and increase with the second "1." The medical device corresponding to the third bit in the bitmap 660 would therefore have the slot index of "2." Medical devices corresponding to subsequent bits would determine their respective slot indexes using the same technique.

In cases where the bitmap 660 is too large to fit in a single communication frame 600 (e.g., in a system having over 1000 medical implants, but only 1000 slots per communication frame 600), the bitmap 660 may be divided among various segments. For a given communication frame 600, the segment is identified by the segment number field 630. (For example, the value of the segment number fields 630 in the first, second, and third segments may be "1," "2," and "3," respectively.) For a given segment, the value of the starting address field 640 can identify the starting address (or starting bit location in the bitmap) corresponding to the first bit the portion of the bitmap 660 included in the segment, thereby indicating where, in the bitmap, the bitmap bits begin in a communication frame 600 for the segment. The starting slot index field 650 can include a running slot index so that, for a given segment, medical implants corresponding to bits included in the communication frame 6004 that segment can keep track of where the slot index begins and accurately calculate their slot index. For example, if a group has three segments, each having have 1000 bits of a 3000-bit bitmap 660, then the starting address field 640 may have a value of 1001, and if no medical implants in the first segment were selected for the group, the starting slot index field 650 would indicate how many medical implants of the first segment where included in the group. (E.g., if no medical implants were selected, the value of the starting slot index field in the second segment would be "a") Any medical implant whose address is included in the bitmap 660 (or portion of the bitmap 660, if the bitmap is segmented) of a given communication frame 600 can send back an ACK message after receiving the communication frame 600 (schedule message). In some embodiments, it may not matter if the communication frame 600 is a retransmission. The interrogator device can keep sending a communication frame 600 under the bitmap method until it has received ACK messages from all the medical implants corresponding to bits of the bitmap 660 (or portion of the bitmap 660) included in the communication frame 600 or until its maximum retransmission limit has been reached.

Figure 7:
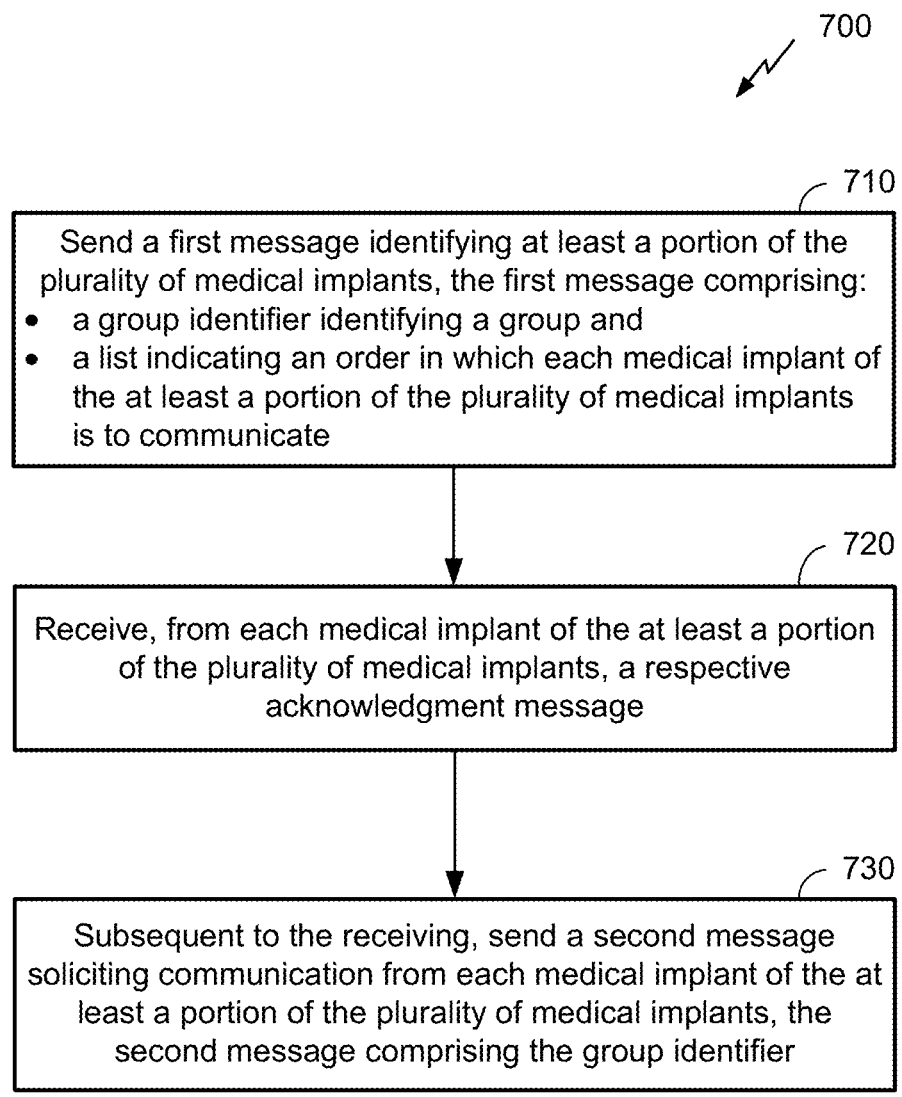
FIG. 7 is a flow diagram of a method of implementing a selection protocol between an interrogator device and a plurality of medical implants of the medical implant system, according to an embodiment.

FIG. 7 is a flow diagram of a method 700 of implementing a selection protocol between an interrogator device and a plurality of medical implants of the medical implant system, according to an embodiment. One or more of the functions of the blocks of the method 700 may be executed by software and/or hardware components of an interrogator device, such as the interrogator device 140 illustrated in FIG. 8 and described in more detail below.

At block 710, the first message is sent, identifying at least a portion of the plurality of medical implants, where the first message comprises a group identifier identifying a group, and a list. The list indicates in order in which each medical implant of the at least a portion of the plurality of medical implants is to communicate. As discussed above, in the preconfigured group method, the group identifier may correspond to a group ID programmed into one or more medical implants of the at least a portion of the plurality of medical implants during manufacture. Otherwise, the interrogator device can engage in dynamic group selection such that the list can designate each medical implant of the at least a portion of the plurality of medical implants to the group. Under the sub-addressing method, the list can comprise an address list, and an order of the addresses in the address list can be indicative of a slot index for each of the at least a portion of the plurality of medical implants to transmit data to the interrogator device. Under the individual selection method, the list can comprise a list of medical implants to be turned on or off. Under the bitmap method, the list can comprise a bitmap having a bit corresponding to each medical implant of the at least a portion of the plurality of medical implants, where the bit indicates whether each respective medical implant is turned off or on. Further, under the bitmap method, the bitmap may further indicate a slot index for each medical implant turned on in the bitmap.

Means for performing the functionality at block 710 can comprise a bus 805, processing unit(s) 810, communication interface 840, antenna(s) 845, memory 850, and/or other components of an interrogator device 140, as shown in FIG. 8 and described herein below.

At block 720, the functionality comprises receiving, from each medical implant of the at least a portion of the plurality of medical implants, a respective acknowledgment message. As noted previously, under some embodiments, the interrogator device may not proceed with a trigger message to the newly formed group without first receiving an ACK message from each of the affected medical implants. Means for performing the functionality at block 720 can comprise a bus 805, processing unit(s) 810, communication interface 840, antenna(s) 845, memory 850, and/or other components of an interrogator device 140, as shown in FIG. 8 and described herein below.

At block 730, subsequent to the receiving at block 720, a second message is sent, soliciting communication from each medical implant of the at least a portion of the plurality of medical implants. Here, the second message comprises the group identifier. In this manner, each medical implant of the group can identify that the interrogator device has solicited communication from the medical implant, and the medical implant will know its respective time slot during the uplink communication. Some embodiments may comprise, subsequent to sending the second message, receiving data from one or more medical implants of the at least a portion of the plurality of medical implants. Means for performing the functionality at block 730 can comprise a bus 805, processing unit(s) 810, communication interface 840, antenna(s) 845, memory 850, and/or other components of an interrogator device 140, as shown in FIG. 8 and described herein below.

FIG. 8 is a simplified block diagram of a interrogator device 140, according to an embodiment. The interrogator device 140 may comprise a "skin patch" (similar to the interrogator device of FIG. 1) or other device configured to perform one or more of the functions of an interrogator device of a biological measurement and stimulation system as described in embodiments herein. FIG. 8 is meant only to provide a generalized illustration of various components, any or all of which may be included or omitted as appropriate. The interrogator device 140 may be configured to execute one or more functions of the methods described herein, such as the methods corresponding to the functionality described in relation to FIG. 7. It can be further noted that the interrogator device 140 may be configured to receive measurements from and/or stimulate a body part utilizing one or more medical implants with which the interrogator device 140 is in wireless communication, as described in the embodiments above. In some embodiments, the particular measurements taken and/or stimulations may be determined by the interrogator device 140 itself, and/or be determined by another device (such as a medical device, mobile phone, tablet, etc.) with which the interrogator device 140 is in communication. A person of ordinary skill in the art will understand that, for the sake of simplicity, some components (e.g., power source, physical housing, etc.) are not shown.

The interrogator device 140 is shown comprising hardware elements that can be electrically coupled via a bus 805 (or may otherwise be in communication, as appropriate). The hardware elements may include a processing unit(s) 810 which may comprise without limitation one or more general-purpose processors, one or more special-purpose processors (such as digital signal processing (DSP) chips, graphics acceleration processors, application specific integrated circuits (ASICs), and/or the like), and/or other logic, processing structure, or means, which can be configured to perform one or more of the methods described herein.

Depending on desired functionality, the interrogator device 140 also may comprise one or more input devices 820, which may comprise without limitation one or more, touch sensors, buttons, switches, and/or more sophisticated input components, which may provide for user input, which may enable the system to power on, configure operation settings, and/or the like. Output device(s) 830 may comprise, without limitation, light emitting diode (LED)s, speakers, and/or more sophisticated output components, which may enable feedback to a user, such as an indication the implant system has been powered on, is in a particular state, is running low on power, and/or the like.

The interrogator device 140 might also include a communication interface 840 and one or more antennas 845. This communication interface 840 and antenna(s) 845 can enable the interrogator device 140 to communicate with and optionally power the medical implants of the wireless medical implant system. The one or more antennas 845 can be configured to, when power properly, generate particular signals and/or fields to communicate with and/or power the medical implants, including communicating medical implant selection methods as described herein. As previously indicated, medical implants in some embodiments may communicate using RF backscatter, in which case the interrogator device 140 may transmit an RF carrier signal, modulated by the medical implants during uplink communications.

The communication interface 840 may further enable the interrogator device 140 to communicate with one or more devices outside the biological measurement and stimulation system to which the interrogator device 140 belongs, such as a medical device, mobile phone, tablet, etc. In some embodiments, the one or more devices may execute a software application that provides a user interface (e.g., a graphical user interface) for configuring and/or managing the operation of the interrogator device 140. The communication interface may include connectors and/or other components for wired communications (e.g., universal serial bus (USB) Ethernet, optical, and/or other communication). Additionally or alternatively, the communication interface 840 and optionally the antenna(s) 845 may be configured to provide wireless communications (e.g., via Bluetooth, Bluetooth low energy, Institute of Electrical and Electronics Engineers (IEEE) 802.11, IEEE 802.15.4 (or ZIGBEE), WIFI, WiMAX, cellular communications, infrared, etc.). As such, the communication interface 840 may comprise without limitation a modem, a network card, an infrared communication device, a wireless communication device, and/or a chipset.

The interrogator device 140 may further include and/or be in communication with a memory 850. The memory 850 may comprise, without limitation, local and/or network accessible storage such as optical, magnetic, solid-state storage (e.g., random access memory ("RAM") and/or a read-only memory ("ROM")), or any other medium from which a computer can read instructions and/or code. The memory 850 may therefore make the interrogator device 140 can be programmable, flash-updateable, and/or the like. Such storage devices may be configured to implement any appropriate data stores, including without limitation, various file systems, database structures, and/or the like.

The memory 850 of the interrogator device 140 also can comprise software elements (not shown), including an operating system, device drivers, executable libraries, and/or other code, such as one or more application programs, which may comprise computer programs provided by various embodiments, and/or may be designed to implement methods, and/or configure systems, provided by other embodiments, as described herein. For example, one or more procedures described with respect to the functionality discussed above might be implemented as computer code and/or instructions executable by the interrogator device 140 (and/or processing unit(s) 810 of the interrogator device 140). The memory 850 may therefore comprise non-transitory machine-readable media having the instructions and/or computer code embedded therein/thereon.

FIG. 9 is a simplified block diagram of a medical implant 130, according to an embodiment. The medical implant 130 may comprise a "neurograin" (similar to the medical implants 130 of FIG. 1) or other device configured to perform one or more of the functions of a medical implant of a biological measurement and stimulation system as described in embodiments herein. FIG. 9 is meant only to provide a generalized illustration of various components, any or all of which may be included or omitted as appropriate. It can be further noted that the medical implant 130 may be configured to take measurements and/or stimulate a body part as directed by an interrogator device 140 using communications such as those described in the embodiments herein. A person of ordinary skill in the art will understand that, for the sake of simplicity, some components (e.g., power source, physical housing, etc.) are not shown. It will be understood that, in most embodiments, hardware and/or software optimizations may be made to help minimize power consumption.

The medical implant 130 is shown comprising hardware elements that can be electrically coupled via a bus 905, or may otherwise be in communication, as appropriate. The hardware elements may include a processing unit(s) 910 which may comprise without limitation one or more general-purpose processors, one or more special-purpose processors, and/or other logic, processing structure, or means, which can be configured to perform one or more of the methods described herein. The processing unit(s) 810, may further include one or more counters (implemented in hardware and/or software) as described herein.

The medical implant 130 may further include and/or be in communication with a memory 920. As with other components of the medical implant 130, the memory 920 may be optimized for minimum power consumption. In some embodiments, the memory 920 may be Incorporated into the processing unit(s) 910. Depending on desired functionality, the memory (which can include a non-transitory computer-readable medium, such as a magnetic, optical, or solid-state medium) may include computer code and/or instructions executable by the processing unit(s) 910 to perform one or more functions described in the embodiments herein.

A communication interface 930 and antenna(s) 935 can enable the medical implant 130 to wirelessly communicate the interrogator device, as described herein. The antenna(s) 935 may comprise a coiled or other antenna configured to draw power from communications and/or other signals or fields generated by the interrogator device, powering the medical implant 130. In some embodiments, the medical implant 130 may further include an energy storage medium (e.g., a battery, capacitor, etc.) to store energy captured by the antenna(s) 935. In some embodiments, the communication interface 930 and antenna(s) 935 may be configured to the interrogator device using RF backscatter.

The stimulator(s) 940 of the medical implant 130 can enable the medical implant 130 to provide stimulation to a body part (e.g., biological tissue) in which the medical implant 130 is implanted. As such, the stimulator(s) 940 may comprise an electrode, light emitting diode (LED), and/or other component configured to provide electrical, optical, and/or other stimulation. The processing unit(s) 910 may control the operation of the stimulator(s) 940, and may therefore control the timing, amplitude, and/or other stimulation provided by the stimulator(s) 940.

The sensor(s) 950 may comprise one or more sensors configured to receive input from a body part (e.g., biological tissue), in which the medical implant 130 is implanted. Sensors may therefore be configured to sense electrical impulses, pressure, temperature, light, conductivity/resistivity, and/or other aspects of a body part. As described herein, embodiments may enable medical implant 130 to provide this information, via the communication interface 930, to an interrogator device. Depending on desired functionality, information received by the sensor(s) 950 may be encrypted, compressed, and/or otherwise processed before it is transmitted via the communication interface 930.

It will be apparent to those skilled in the art that substantial variations may be made in accordance with specific requirements. For example, customized hardware might also be used, and/or particular elements might be implemented in hardware, software (including portable software, such as applets, etc.), or both. Further, connection to other computing devices such as network input/output devices may be employed.

The methods, systems, and devices discussed herein are examples. Various embodiments may omit, substitute, or add various procedures or components as appropriate. For instance, features described with respect to certain embodiments may be combined in various other embodiments. Different aspects and elements of the embodiments may be combined in a similar manner. The various components of the figures provided herein can be embodied in hardware and/or software. Also, technology evolves and, thus, many of the elements are examples that do not limit the scope of the disclosure to those specific examples.

It has proven convenient at times, principally for reasons of common usage, to refer to such signals as bits, information, values, elements, symbols, characters, variables, terms, numbers, numerals, or the like. It should be understood, however, that all of these or similar terms are to be associated with appropriate physical quantities and are merely convenient labels. Unless specifically stated otherwise, as is apparent from the discussion above, it is appreciated that throughout this Specification discussions utilizing terms such as "processing," "computing," "calculating," "determining," "ascertaining," "identifying," "associating," "measuring," "performing," or the like refer to actions or processes of a specific apparatus, such as a special purpose computer or a similar special purpose electronic computing device. In the context of this Specification, therefore, a special purpose computer or a similar special purpose electronic computing device is capable of manipulating or transforming signals, typically represented as physical electronic, electrical, or magnetic quantities within memories, registers, or other information storage devices, transmission devices, or display devices of the special purpose computer or similar special purpose electronic computing device.

Terms, "and" and "or" as used herein, may include a variety of meanings that also is expected to depend at least in part upon the context in which such terms are used. Typically, "or" if used to associate a list, such as A, B, or C, is intended to mean A, B, and C, here used in the inclusive sense, as well as A, B, or C, here used in the exclusive sense. In addition, the term "one or more" as used herein may be used to describe any feature, structure, or characteristic in the singular or may be used to describe some combination of features, structures, or characteristics. However, it should be noted that this is merely an illustrative example and claimed subject matter is not limited to this example. Furthermore, the term "at least one of" if used to associate a list, such as A, B, or C, can be interpreted to mean any combination of A, B, and/or C, such as A, AB, AA, AAB, AABBCCC, etc.

Having described several embodiments, various modifications, alternative constructions, and equivalents may be used without departing from the spirit of the disclosure. For example, the above elements may merely be a component of a larger system, wherein other rules may take precedence over or otherwise modify the application of the invention. Also, a number of steps may be undertaken before, during, or after the above elements are considered. Accordingly, the above description does not limit the scope of the disclosure.

What is claimed is:

1. A method of implementing a selection protocol between an interrogator device and a plurality of medical implants of a medical implant system, the method comprising:

sending, with the interrogator device via a local wireless interface of the interrogator device, a first message identifying at least a portion of the plurality of medical implants, the first message comprising:
a group identifier identifying a group, and
a list indicating an order in which each medical implant of the at least a portion of the plurality of medical implants is to communicate;

receiving, from each medical implant of the at least a portion of the plurality of medical implants, a respective acknowledgement message; and subsequent to the receiving, sending, via the local wireless interface, a second message soliciting communication from each medical implant of the at least a portion of the plurality of medical implants, the second message comprising the group identifier.

2. The method of claim 1, wherein the group identifier corresponds to a group identifier programmed into one or more medical implants of the at least a portion of the plurality of medical implants during manufacture.

3. The method of claim 1, wherein the list designates each medical implant of the at least a portion of the plurality of medical implants to the group.

4. The method of claim 3, wherein the list comprises an address list, and an order of addresses in the address list is indicative of a slot index for each of the at least a portion of the plurality of medical implants to transmit data to the interrogator device.

5. The method of claim 1, wherein the list comprises a list of medical implants to be turned on or off.

6. The method of claim 1, wherein the list comprises a bitmap having a bit corresponding to each medical implant of the at least a portion of the plurality of medical implants, the bit indicating whether each respective medical implant is turned on or off.

7. The method of claim 6, wherein the bitmap further indicates a slot index for each medical implant turned on in the bitmap.

8. The method of claim 1, further comprising, subsequent to sending the second message, receiving data from one or more medical implants of the at least a portion of the plurality of medical implants.

9. An interrogator device for implementing a selection protocol when communicating with a plurality of medical implants of a medical implant system, the interrogator device comprising:
a local wireless interface; and
a processing unit communicatively coupled with the local wireless interface and configured to cause the interrogator device to:
send, via the local wireless interface, a first message identifying at least a portion of the plurality of medical implants, the first message comprising:
a group identifier identifying a group, and
a list indicating an order in which each medical implant of the at least a portion of the plurality of medical implants is to communicate;
receive, from each medical implant of the at least a portion of the plurality of medical implants, a respective acknowledgement message; and
subsequent to the receiving, send, via the local wireless interface, a second message soliciting communication from each medical implant of the at least a portion of the plurality of medical implants, the second message comprising the group identifier.

10. The interrogator device of claim 9, wherein the interrogator device is configured to cause the group identifier to correspond to a group identifier programmed into one or more medical implants of the at least a portion of the plurality of medical implants during manufacture.

11. The interrogator device of claim 9, the interrogator device is configured to cause the list to designate each medical implant of the at least a portion of the plurality of medical implants to the group.

12. The interrogator device of claim 11, wherein the interrogator device is configured to:
include, in the list, an address list, and
cause an order of addresses in the address list to indicate a slot index for each of the at least a portion of the plurality of medical implants to transmit data to the interrogator device.

13. The interrogator device of claim 9, wherein the interrogator device is configured to cause the list to comprise a list of medical implants to be turned on or off.

14. The interrogator device of claim 9, wherein the interrogator device is configured to cause the list to comprise a bitmap having a bit corresponding to each medical implant of the at least a portion of the plurality of medical implants, the bit indicating whether each respective medical implant is turned on or off.

15. The interrogator device of claim 14, wherein the interrogator device is configured to cause the bitmap to further indicate a slot index for each medical implant turned on in the bitmap.

16. The interrogator device of claim 9, wherein the processing unit is further configured to cause the interrogator device to, subsequent to sending the second message, receive data from one or more medical implants of the at least a portion of the plurality of medical implants.

17. An apparatus for implementing a selection protocol with a plurality of medical implants of a medical implant system, the apparatus comprising:
means for sending a first message identifying at least a portion of the plurality of medical implants, the first message comprising:
a group identifier identifying a group, and
a list indicating an order in which each medical implant of the at least a portion of the plurality of medical implants is to communicate;
means for receiving, from each medical implant of the at least a portion of the plurality of medical implants, a respective acknowledgement message; and
means for sending, subsequent to the receiving, a second message soliciting communication from each medical implant of the at least a portion of the plurality of medical implants, the second message comprising the group identifier.

18. The apparatus of claim 17, further comprising means for causing the group identifier to correspond to a group identifier programmed into one or more medical implants of the at least a portion of the plurality of medical implants during manufacture.

19. The apparatus of claim 17, further comprising means for causing the list to designate each medical implant of the at least a portion of the plurality of medical implants to the group.

20. The apparatus of claim 19, further comprising means for:
causing the list to comprise an address list, and
causing an order of addresses in the address list to indicate a slot index for each of the at least a portion of the plurality of medical implants to transmit data.

21. The apparatus of claim 17, further comprising means for causing the list to comprise a list of medical implants to be turned on or off.

22. The apparatus of claim 17, further comprising means for causing the list to comprise a bitmap having a bit corresponding to each medical implant of the at least a portion of the plurality of medical implants, the bit indicating whether each respective medical implant is turned on or off.

23. The apparatus of claim 22, further comprising means for causing the bitmap to further indicate a slot index for each medical implant turned on in the bitmap.

24. The apparatus of claim 17, further comprising means for, subsequent to sending the second message, receiving data from one or more medical implants of the at least a portion of the plurality of medical implants.

25. A non-transitory computer-readable medium having instructions embedded thereon for implementing a selection protocol between an interrogator device and a plurality of medical implants of a medical implant system, the instructions including computer code for:
- sending a first message identifying at least a portion of the plurality of medical implants, the first message comprising:
  - a group identifier identifying a group, and
  - a list indicating an order in which each medical implant of the at least a portion of the plurality of medical implants is to communicate;
- receiving, from each medical implant of the at least a portion of the plurality of medical implants, a respective acknowledgement message; and
- subsequent to the receiving, sending a second message soliciting communication from each medical implant of the at least a portion of the plurality of medical implants, the second message comprising the group identifier.

26. The non-transitory computer-readable medium of claim 25, wherein the instructions further comprise computer code for causing the group identifier to correspond to a group identifier programmed into one or more medical implants of the at least a portion of the plurality of medical implants during manufacture.

27. The non-transitory computer-readable medium of claim 25, wherein the instructions further comprise computer code for causing the list to designate each medical implant of the at least a portion of the plurality of medical implants to the group.

28. The non-transitory computer-readable medium of claim 27, wherein the instructions further comprise computer code for causing the list to comprise an address list, and an order of addresses in the address list is indicative of a slot index for each of the at least a portion of the plurality of medical implants to transmit data to the interrogator device.

29. The non-transitory computer-readable medium of claim 25, wherein the instructions further comprise computer code for causing the list to comprise a list of medical implants to be turned on or off.

30. The non-transitory computer-readable medium of claim 25, wherein the instructions further comprise computer code for causing the list to comprise a bitmap having a bit corresponding to each medical implant of the at least a portion of the plurality of medical implants, the bit indicating whether each respective medical implant is turned on or off.

* * * * *